US009844625B2

(12) United States Patent
Schneider et al.

(10) Patent No.: US 9,844,625 B2
(45) Date of Patent: Dec. 19, 2017

(54) MACROPOROUS FILTRATION MEMBRANE

(75) Inventors: Frank Schneider, Wuppertal (DE); Martin Czernik, Leverkusen (DE); Walter Stripp, Wuppertall (DE); Ramona Tatsch, Velbert (DE)

(73) Assignee: 3M Innovative Properties Company, St. Paul, MN (US)

(*) Notice: Subject to any disclaimer, the term of this patent is extended or adjusted under 35 U.S.C. 154(b) by 79 days.

(21) Appl. No.: 14/110,947

(22) PCT Filed: Mar. 29, 2012

(86) PCT No.: PCT/EP2012/055573
§ 371 (c)(1),
(2), (4) Date: Oct. 23, 2013

(87) PCT Pub. No.: WO2012/139896
PCT Pub. Date: Oct. 18, 2012

(65) Prior Publication Data
US 2014/0039415 A1     Feb. 6, 2014

(30) Foreign Application Priority Data
Apr. 13, 2011 (EP) .................................. 11162177

(51) Int. Cl.
*B01D 71/68* (2006.01)
*A61M 5/165* (2006.01)
(Continued)

(52) U.S. Cl.
CPC .......... *A61M 5/165* (2013.01); *A61M 5/1411* (2013.01); *A61M 5/16804* (2013.01);
(Continued)

(58) Field of Classification Search
None
See application file for complete search history.

(56) References Cited

U.S. PATENT DOCUMENTS 4,263,017 A * 4/1981 Karn .................. B01D 53/22
                                      210/321.74
4,267,047 A * 5/1981 Henne ................. B01D 69/04
                                      210/490

(Continued)

FOREIGN PATENT DOCUMENTS

EP    0361085 A1    9/1988
EP    0297744       1/1989

(Continued)

OTHER PUBLICATIONS

Van Rijn et al., "Nanosieves with microsystem technology for microfiltration applications", Nanotechnology, 9, Dec. 1998, pp. 343-345.*

(Continued)

*Primary Examiner* — Michael H Wilson
*Assistant Examiner* — Katherine Will
(74) *Attorney, Agent, or Firm* — Scott A. Baum

(57) ABSTRACT

Hydrophilic flat-sheet membrane based on a hydrophobic first polymer from the group consisting of aromatic sulfone polymers and a hydrophilic second polymer, wherein the membrane has a thickness in the range between 30 and 200 μm, a first and a second surface and a supporting layer having a three-dimensional sponge-like network structure, wherein the supporting layer has a first cover layer on the side thereof facing the first surface and a second cover layer on the side thereof facing the second surface, which cover layers are formed integrally with the supporting layer, and wherein the first and second surfaces have approximately oval or circular openings which penetrate the first and second cover layers, respectively, and are connected to the supporting layer, wherein the average diameter of the openings in the surfaces differ by a factor of less than 2, wherein the three-dimensional network structure of the supporting layer is made up of thick branches and a continuous pore (Continued)

Figure 6:
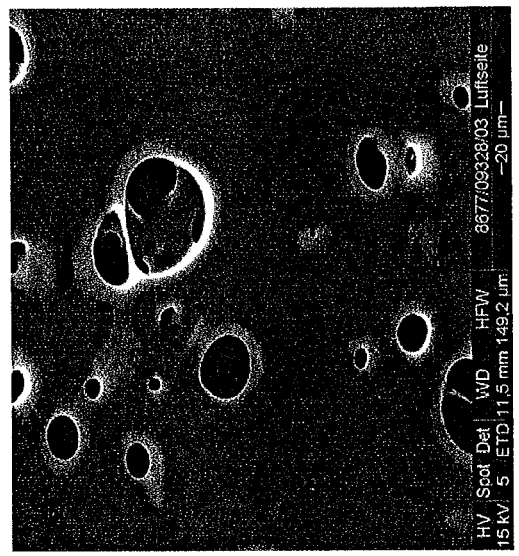

system, and the predominant proportion of the branches have a diameter of at least 0.5 μm at the thinnest point thereof and wherein the pores in the supporting layer are larger than the openings in the surfaces.

15 Claims, 10 Drawing Sheets

(51) Int. Cl.
*B01D 67/00* (2006.01)
*B01D 69/02* (2006.01)
*A61M 5/14* (2006.01)
*A61M 5/168* (2006.01)

(52) U.S. Cl.
CPC ......... *B01D 67/0009* (2013.01); *B01D 69/02* (2013.01); *B01D 71/68* (2013.01); *A61M 2005/1652* (2013.01); *A61M 2005/1657* (2013.01); *A61M 2205/7527* (2013.01); *B01D 2325/02* (2013.01); *B01D 2325/021* (2013.01)

(56) References Cited

U.S. PATENT DOCUMENTS

| | | |
|---|---|---|
| 4,943,374 A | 7/1990 | Heininger et al. |
| 5,240,862 A | 8/1993 | Koenhen et al. |
| 5,846,422 A | 12/1998 | Ditter et al. |
| 5,886,059 A | 3/1999 | Wang |
| 5,906,742 A | 5/1999 | Wang et al. |
| 5,979,670 A | 11/1999 | Ditter et al. |
| 6,054,899 A | 4/2000 | Ke |
| 6,056,903 A | 5/2000 | Greenwood et al. |
| 2004/0043224 A1* | 3/2004 | Sternberg .............. A61M 5/165 428/421 |
| 2008/0197072 A1* | 8/2008 | Ansorge ............. B01D 67/0011 210/500.41 |
| 2010/0219122 A1* | 9/2010 | Ogawa .................. B01D 69/02 210/500.23 |
| 2010/0224553 A1* | 9/2010 | Ansorge ............... B01D 61/145 210/490 |

FOREIGN PATENT DOCUMENTS

| | | | |
|---|---|---|---|
| EP | 0543355 B1 | 5/1993 | |
| EP | 0882494 B1 | 12/1998 | |
| EP | 0696935 B1 | 11/2001 | |
| EP | 2113298 A1 * | 11/2009 | ......... B01D 67/0011 |
| JP | 62-071802 | 4/1987 | |
| JP | H02-152528 A | 6/1990 | |
| JP | H04-090832 A | 3/1992 | |
| JP | H05-154360 | 6/1993 | |
| JP | H07-163849 A | 6/1995 | |
| JP | 2004-098027 | 4/2004 | |
| JP | 2008-221050 | 9/2008 | |
| WO | WO 96/40421 A1 | 12/1996 | |
| WO | WO 02/07854 A1 | 1/2002 | |

OTHER PUBLICATIONS

Van Rijn et al., "Nanosieves with microsystem technology for microfiltration applications," Dec. 1998, Nanotechnology, 9, 343-345.*

* cited by examiner

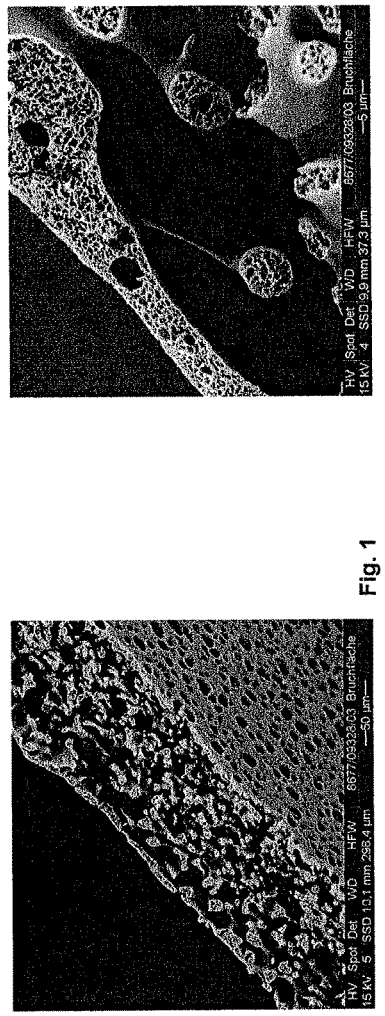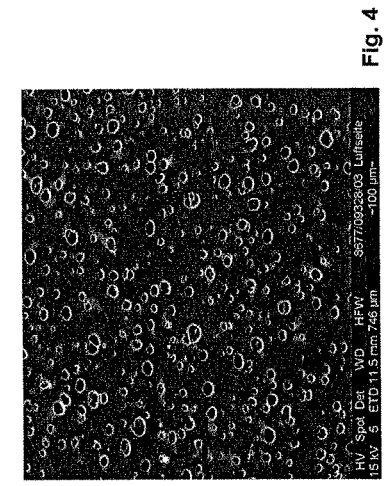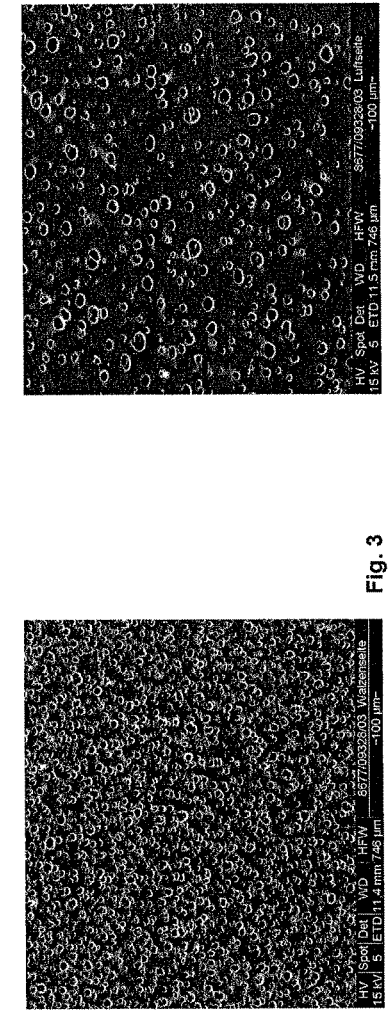

MACROPOROUS FILTRATION MEMBRANE

The invention relates to a hydrophilic, macroporous filtration membrane in the form of a flat-sheet membrane based on a film-forming hydrophobic first polymer from the group consisting of aromatic sulfone polymers and a hydrophilic second polymer, wherein the membrane has a first and a second surface and a supporting layer extending between the surfaces and having a three-dimensional sponge-like network structure.

Microporous polymer membranes are used in the most varied industrial, pharmaceutical, and medical applications for precision filtration. In these applications, membrane separation processes are becoming increasingly important, since these processes offer the advantage that the materials to be separated are not thermally stressed and certainly not damaged. Microfiltration membranes enable for example the removal of fine particles or microorganisms having sizes down to the submicron range, and are therefore suitable for the production of purified water for use in laboratories or for the semiconductor industry. Numerous other applications of membrane separation processes are known from the beverage industry, biotechnology, or from wastewater technology.

In most cases, membranes with a pronounced asymmetry are used, which membranes have a separating layer and a microporous supporting structure adjoining thereto, which supporting structure has coarser pores in comparison to the separating layer. The pores in the separating layer thereby determine the actual separation properties of the membrane, i.e. the size of the particles or molecules that are retained by the membrane is controlled by the size of the pores in the separating layer. During application, membranes of this type are used in many cases such that they are flowed onto from the more open-pored side and thus the microporous supporting layer functions as a prefilter for the separating layer. By this means, the dirt-loading capacity of the membrane is increased. A fluid which thus flows through the membrane enters first into the larger pores and then into the small pores of the separating layer. By this means, particles that are contained in the fluid are retained in the coarse-pored supporting layer before they can reach the separating layer and clog it.

For numerous membrane applications, sulfone polymers such as polysulfone or polyethersulfone represent a membrane material that is often used, not least because of their high chemical stability, their high temperature stability, or the sterilization capability of membranes produced therefrom. However, these polymers are hydrophobic polymers, which limits the use thereof for the filtration of aqueous media. In addition, it is known that membranes made from hydrophobic materials have a strong, nonspecific adsorptivity, which often results during use in a fast coating of the membrane surface with preferably higher-molecular-weight components of the liquid to be filtered and as a consequence results in a degradation of the permeability.

U.S. Pat. No. 6,056,903 relates to microporous polyethersulfone membranes having an effective pore size of at least 0.01 μm and preferably a pore size in the range from approximately 0.1 to 20 μm. The membranes of U.S. Pat. No. 6,056,903 are, however, hydrophobic and have an essentially symmetrical pore structure across the skinless wall.

Membranes made of polysulfone and having a pronounced asymmetry are likewise described in EP-A-0 696 935, U.S. Pat. No. 5,846,422, and U.S. Pat. No. 5,979,670. These membranes are hydrophobic due to the sole use of polyethersulfone. On the surface with narrower pores, they have an average pore diameter of at least 1.2 μm, wherein, starting from this surface, the membrane wall has an isotropic area in which the pores have an essentially constant size. The pores of the second surface are larger than the pores of the first surface by a factor of at least 2, preferably at least 3 or even 6. These membranes are intended to be used e.g. for analytic or diagnostic processes in which particular value is placed on high throughput speeds. Due to the sole use of polyethersulfone as the polymer forming the membrane structure, these membranes are hydrophobic and thus are not spontaneously wettable with water. As a result of these hydrophobic properties, these membranes tend toward blockages in the inner membrane structure during use as a result of an adsorption of substances contained in the liquid to be filtered.

U.S. Pat. No. 5,906,742 also relates to integrally asymmetric membranes based on polysulfones, the wall thereof having an isotropic area with essentially constant pore diameters adjoining the first surface with a microporous skin, said isotropic area being followed in direction to the second surface by an asymmetric area with pores that increase in size in the direction of the second surface. The membranes of U.S. Pat. No. 5,906,742 are hydrophilic due to mixing a hydrophilic polymer with the polysulfone. The pores in the microporous skin adjoining the isotropic area have an average diameter exceeding approximately 1 μm, and the pores in the second surface are larger by a factor of greater than 2, preferably greater than 3 to 6 or higher. Without taking the surfaces into consideration, the asymmetry is even more pronounced, and is at least 10:1 or 20:1, or even up to 100:1 or 200:1. The membranes of U.S. Pat. No. 5,906,742 are thus asymmetric to a high degree in the wall thereof. However, the pronounced asymmetry in connection with large pore sizes exerts negative effects on the mechanical properties of the membranes and in particular leads to low compressibility of these membranes.

U.S. Pat. No. 5,886,059 relates to a polyethersulfone membrane for microfiltration, wherein the membrane has a pronounced asymmetric structure. It has a skin with relatively small pores on a first side thereof and, starting from this side, pore sizes increasing across the entire membrane wall up to the other, second membrane side, wherein the pores on the second side are larger than the pores in the skin on the first side by a factor of 50 to 10000. Membranes with a structure of this type are susceptible to mechanical damage with regard to the layer with the smallest pores, i.e. the separating layer, which is located on the surface of the membrane. The membranes also have only a moderate mechanical stability due to the specific asymmetric structure.

WO 02/07854 discloses a blood collection system having a main filter for removing leukocytes. The main filter consists of a membrane made of polyethersulfone, which has a layered structure, a first skin surface and a second skin surface, as well as an inner pore structure with cellular pores, wherein the membrane likewise has a pronounced asymmetric pore structure across the wall. The cells of the inner pore structure adjacent to the first skin surface are smaller than the cells of the inner pore structure adjacent to the second skin surface, wherein the majority of the pores in the first surface have a diameter between approximately 12 and 28 μm.

Uses in the sector of medical technology relate among others to devices for diagnostic purposes, as are described e.g. in U.S. Pat. No. 5,240,862. The devices from U.S. Pat. No. 5,240,862 are systems for separation of blood, in which an asymmetric membrane is in intimate contact with a collector membrane. In the application, whole blood is applied to the coarser-pored side of the asymmetric membrane, and blood cells are retained in the large pores of the asymmetric membrane. Blood plasma flows through the membrane and enters the collector membrane. The collector membrane is generally equipped with an analytical detection system so that the plasma can be examined for certain components contained therein.

A specific application of microporous membranes in medical technology relates to filters for the administration of infusion solutions. In this case, open-pored membrane filters are installed in the flow path of the infusion solution in order to maintain a constant passage rate of infusion solutions, such as aqueous sodium chloride, glucose, and lipid solutions, independent of the hydrostatic pressure head, and also to retain potential particles or undissolved material contained in the infusion solution. At the same time, these membrane filters often have the task of separating gas bubbles from infusion solutions. Filters of this type are disclosed for example in EP 0 254 100 B1.

During the administration of infusion solutions, however, there often exists the desire that a fluid column remains in the infusion cannula at the end of the application, and a new infusion bottle can be connected without necessitating a deaeration of the cannula. By this means, the problem of deaerating the infusion cannulae and/or the infusion solutions to be administered can be at least reduced. Therefore, there exists a need for a filter element, which in addition to filtration properties in relation to potential impurities in the infusion solutions also has the property of preventing the infusion cannulae from running dry. Due to the filter element, the inclusion of the filter element in the flow path of the aqueous liquid or the infusion solution should prevent a breaking off of the fluid column formed and enable the formation of sufficiently high fluid columns, for example in capillaries arranged beneath a filter element of this type, so that a sufficient fluid column thus remains standing in the infusion tube. At the same time, the filter element should have a low hydraulic resistance for the passage of liquids. In addition, it should have a high mechanical stability. It is therefore the object of the present invention to provide a suitable filter element for an application of this type.

The object is achieved by a hydrophilic, macroporous filtration membrane in the form of a flat-sheet membrane based on a film-forming hydrophobic first polymer from the group consisting of aromatic sulfone polymers and also a hydrophilic second polymer, wherein the membrane has a first and a second surface and a supporting layer extending between the surfaces and having a three-dimensional sponge-like network structure, wherein the supporting layer has a first cover layer on the side thereof facing the first surface and a second cover layer on the side thereof facing the second surface, which cover layers are formed integrally with the supporting layer, and wherein the first and second surfaces have approximately oval or circular openings which penetrate the first and second cover layers, respectively, and are connected to the supporting layer, wherein the average diameter of the openings in the first surface and the average diameter of the openings in the second surface differ by a factor of less than 2, wherein the three-dimensional network structure of the supporting layer is made up of thick branches and a continuous pore system, and the predominant proportion of the branches have a diameter of at least 0.5 µm at the thinnest point thereof, wherein the pores in the supporting layer are larger than the openings in the surfaces, and wherein the filtration membrane has a thickness in the range between 30 and 200 µm.

Due to the polymers forming it, i.e. due to the fact that the structure of the membrane is formed from a polymer from the group consisting of aromatic sulfone polymers and from a hydrophilic second polymer, the membrane according to the invention has hydrophilic properties and is spontaneously wettable by aqueous liquids, i.e. a water drop on the membrane surface is immediately soaked up by the membrane. Due to this, the membranes are superbly suited for the use, e.g. for the filtration of aqueous liquids.

The present membrane is based on a hydrophobic first polymer from the group consisting of aromatic sulfone polymers and contains in addition a hydrophilic second polymer. Within the context of the present invention, e.g. polysulfones, polyethersulfones, polyphenylene sulfones, poly (aryl ether sulfone)s or copolymers or modifications of these polymers or mixtures of these polymers among themselves are considered as aromatic sulfone polymers. In a preferred embodiment, the hydrophobic first polymer is a polysulfone or a polyethersulfone with the repeating molecular units shown in the following formulas (I) and (II). A polyethersulfone according to formula (II) is used particularly preferably as the hydrophobic first polymer, since it is less hydrophobic than, for example, polysulfone.

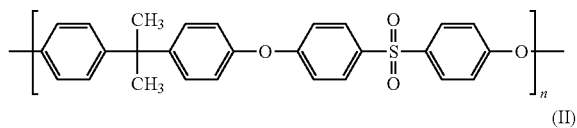

(I)

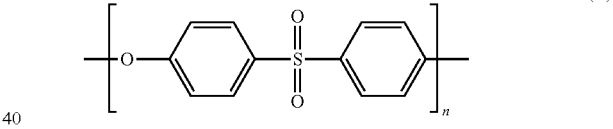

(II)

Advantageously, long-chain polymers are used as the hydrophilic second polymer, which polymers have a good compatibility with the hydrophobic first polymer and provide repeating polymer units that are hydrophilic per se. These are preferably hydrophilic polymers of the type that have an average molecular weight $M_w$ of more than 10000 daltons. The polymers used as the hydrophilic second polymer simultaneously have, in the process of the production of the membrane according to the invention, the object of increasing the viscosity of the homogeneous spinning solution, i.e. to function as thickeners, for which reason these polymers are also often designated as thickeners. In addition, these polymers function as pore-forming agents or nucleating agents during the formation of the membrane structure. The hydrophilic second polymer is preferably a polyvinylpyrrolidone, a polyethylene glycol, a polyvinyl alcohol, a polyglycol monoester, a polysorbate such as polyoxyethylene sorbitan monooleate, a polyacrylate, a carboxyl methylcellulose, a polyacrylic acid or a modification or copolymer of these polymers. The hydrophilic second polymer is particularly preferably a polyvinylpyrrolidone. It is also possible in a further preferred embodiment to use mixtures of different hydrophilic polymers, and in particular mixtures of hydrophilic polymers with different molecular weights, e.g. mixtures of polymers whose molecular weights differ by a factor of 5 or more. The concentration of the hydrophilic second polymer in the membrane according to the invention is preferably 0.5 to 7 wt. % relative to the weight of the membrane. These polymers can if necessary be chemically or physically modified in the membrane. Thus, polyvinylpyrrolidone can subsequently be crosslinked e.g. by high-energy irradiation and thus made water insoluble.

Additives can be used to modify the surface properties of the membranes, which influence the stability of the membrane, the color, or the adsorption or absorption capability. Additives are also possible that control the charge of the membrane, e.g. impart anionic or cationic character to the membrane. The membrane can preferably further contain a hydrophilic third polymer, which differs from the hydrophilic second polymer and is particularly preferably a hydrophilically modified aromatic sulfone polymer. Due to the presence of a polymer of this type, the permeability of the membrane in particular as well as the adsorption properties can be favorably influenced and the membranes can be permanently hydrophilic, which then expresses itself, among other ways, in that the membrane can be multiply steam sterilized, and the hydrophilic properties remain essentially unchanged after for example 30 sterilization cycles. In a particularly preferred embodiment, the hydrophilically modified aromatic sulfone polymer can be present in the membrane in a concentration from 1 to 50 wt. % relative to the weight of the membrane, wherein the sum of the polymers results in 100 wt. %. For this purpose, in the method for producing the preferred membranes according to the invention, the polymer component comprises an additional hydrophilic third polymer, which differs from the hydrophilic second polymer and is a hydrophilically modified aromatic sulfone polymer.

The hydrophilically modified aromatic sulfone polymer can be of the type in which hydrophilic functional groups are covalently bound to the sulfone polymer. However, it can also be a copolymer based on a sulfone polymer in which hydrophilic segments are contained, for example a copolymer of a sulfone polymer and a hydrophilic polymer such as polyvinylpyrrolidone or polyethylene glycol. Due to reasons of compatibility, it is particularly advantageous if the hydrophilically modified aromatic sulfone polymer is based on the hydrophobic first aromatic sulfone polymer, i.e. the membrane structure contains a mixture of a hydrophobic first aromatic sulfone polymer and a hydrophilic modification of this polymer. Very good results are achieved when the hydrophilically modified aromatic sulfone polymer is a sulfonated sulfone polymer, wherein said sulfonated sulfone polymer preferably has a degree of sulfonation in the range from 3 to 10%. Membranes that contain a combination of polyethersulfone and sulfonated polyethersulfone have particularly high permeability for water and proteins and also a low tendency for adsorption, e.g. of proteins or the like, and thus a low degree of fouling.

The supporting structure of the present membrane has a three-dimensional network structure, which is made up of thick branches and a continuous pore system having relatively large pores and which resembles a three-dimensional coral structure, wherein the membranes contain, however, no cavern-like pores, which are also designated as finger pores. The predominant proportion, and thereby preferably at least 70% of the branches, have at the thinnest point thereof a diameter on the order of at least 0.5 µm and preferably at least 2 µm. During a more exact examination of the branches by means of scanning electron microscopy, it can be seen that said branches, as is also applicable for the cover layers, have a skin on the outer side thereof and a porous structure in the interior thereof, wherein the skin of the cover layers and of the branches in the supporting structure is smooth, uniform, and even, as determined during examination by means of scanning electron microscopy, and no irregularities such as ridges, craters or the like can be detected at 500 times magnification. Due to this structure of the supporting layer, the membranes have a low hydraulic resistance, since, despite the large proportion of the supporting structure relative to the total thickness of the membranes, the supporting structure contributes at most very little to the hydraulic resistance of the membrane during the passage of aqueous media, due to the relatively large pores.

In a preferred embodiment, the supporting layer has in this context pores with a diameter of at least 1/10 of the membrane thickness. The thickness of the present membranes lies in the range between 30 and 200 µm and preferably between 50 and 150 µm. It has become evident that, at thicknesses of this type of the present membrane, the general through-flow resistance lies at a sufficiently low level and at the same time the mechanical stability of the membrane is sufficiently high, also with regard to the handling thereof during the processing thereof for the production of filters. It was also surprisingly found that membranes with higher membrane thicknesses have a more pronounced asymmetric structure across the membrane, with distinct differences in regard to the average diameters of the openings in the two membrane surfaces, which differ by a factor of more than 2. It has been additionally found that the permeability of the membranes decreases distinctly at higher membrane wall thicknesses.

Due to the structure of the membrane or the morphology thereof, and due to the geometric dimensions thereof, a low level of through-flow resistance and thus high permeability are achieved for the present membrane. High permeability is, however, required so that, e.g. due to the relatively low pressure head above the membrane during the administration of infusion solutions, sufficiently high throughput is achieved. The present membrane preferably has a transmembrane flow for water, $TMF_{H_2O}$, indicating permeability, in the range from 700 to 4000 ml/(cm$^2$·min·bar) and particularly preferably in the range from 1500 to 4000 ml/(cm$^2$·min·bar).

It has become evident that the branches, which form the network structure and the predominant proportion of which have at the thinnest point thereof a diameter on the order of at least 0.5 µm, at the same time ensure a high mechanical stability of the membrane e.g. to compressive stresses or also to tensile loads. Predominant proportion should be understood in the context of the present invention to mean that at least 50% of the branches, which can also be designated as webs, have the minimum diameter according to the invention. Preferably at least 70% of the branches have a diameter of at least 0.5 µm at the thinnest point thereof. Scanning electron microscopic (SEM) images of cross sections of the membranes at a magnification of at least 1000, preferably at least 1500, can serve thereby as a basis for this judgment, by means of which images the branches can be measured.

The structure typical for the membrane according to the invention, with the network structure forming relatively thick branches, is—as was explained—directly observable via scanning electron microscopic images or also transmission electron microscopic images of membrane cross sections and can be compared in this way with the structures of other membranes. Membranes with thick branches are described for example in EP-A-0 882 494 B1, wherein the membranes described there are asymmetric hollow fiber membranes having pore diameters that gradually increase from the outer side to the inner side. EP-A-0 297 744 also discloses microporous structures having a three-dimensional network structure, the branches of which have a diameter on the order of 1 µm. The diameters and lengths of the branches are determined by means of scanning electron microscopic images or alternatively using image analysis evaluation methods. Further, EP-A-0 543 355 B1 also relates to membranes with network-like structures, wherein the membranes disclosed in this document have network structures with comparatively fine branches or fibrils, which have diameters in the range from 0.1 to 0.5 µm.

In a preferred embodiment, the present membranes have a tensile strength of at least 500 cN/mm$^2$ and particularly preferably 700 cN/mm$^2$ relative to the cross section thereof. Likewise, the present membranes are, despite the relatively coarse network structure and relatively thick branches, not brittle, but instead possess a comparatively high elongation at rupture, wherein it is conjectured that the inner pore structure in the branches or the cover layers is also the cause of this. The elongation at rupture in at least one direction of extension of the membrane is preferably at least 30% and particularly preferably at least 40%. Due to the special three-dimensional network structure with thick branches, a high mechanical stability can also be achieved at relatively high volume porosity of the membranes. The volume porosity preferably lies in the range from 65 to 85 vol. %.

The membrane has a cover layer on the first surface thereof and on the second surface thereof, respectively, which cover layer is formed integrally with the supporting layer. The pressure drop or the hydraulic resistance of the membrane during the passage of aqueous liquids can be influenced via the cover layers of the membrane according to the invention. At the same time, it turned out that the height of the fluid columns can be influenced via the formation of the cover layers and in particular via the size of the openings or pores present in the cover layers, which fluid columns remain in capillaries below the filter elements that are formed by the present membranes after a liquid channeled through the filters has completely flowed through the same, that is, the passage has come to a stop. It has been shown that by means of the present membranes, water columns of a height of at least 1 m can be realized in infusion lines below the membrane elements, without allowing a breakthrough of air through the membrane and thereby a break-up of the fluid column underneath the membrane.

The first and second cover layers each preferably have a thickness in the range from approximately 3 to approximately 10 µm. For cover layers with a thickness of less than approximately 3 µm, a sufficient stability of the cover layers is no longer achieved, and a consistent formation of the cover layers is no longer guaranteed. For thicknesses of more than approximately 10 µm, the pressure drop during the flow through the cover layers can be too high and the hydraulic permeability of the membrane is then too low. The thickness of the cover layers can be determined e.g. by measurements using SEM images of cross sections of the membranes according to the invention, wherein SEM images with a magnification of 250 or 500 are suitable.

It is assumed that the surface pores also influence the capillary forces in the membrane when it is wetted with aqueous liquids. It has thereby been shown that it is advantageous if the openings or pores in the surfaces of the present membrane have uniform, on average approximately oval or circular cross sections. Approximately circular openings or pores should be thereby understood in the context of the present invention as openings in which the ratio of the largest axis to the smallest axis of the opening or pore, which axes extend perpendicular to each other and run through the center of the opening or pore, is not greater than 2. At the same time, it is advantageous that the openings or pores in the surfaces of the present membranes have an island-sea structure, in which uniform, on average approximately oval or circular-shaped openings in the surfaces thus form islands in the cover layer and are respectively surrounded by cover layer material. The cover layers respectively form a continuous phase in the form of webs surrounding the openings or pores, which webs lie on the respective surface in one plane. Directly below the surfaces with approximately oval or circular openings, the membrane structure transitions into the three-dimensional network structure having an irregularly formed pore system.

The present membrane thereby differs with respect to the surface structure thereof from membranes in which the network-like structure of the supporting layer extends to at least one of the surfaces, such that the surfaces themselves have a network-like or fibril-like surface structure, as for example is shown for the open-pored side of the pronounced asymmetric membranes described in U.S. Pat. No. 6,054, 899, for the inner side of the hollow fiber membranes of EP-A-361 085, or for the membranes disclosed in EP-A-0 543 355.

With a view to the applications for the present membrane and in particular to the achievement of sufficiently high flow rates through the membrane, the porous proportion of the area of the first surface, i.e. the ratio of the openings or pores in the first surface to the total area of the first surface is, in a preferred embodiment, at least 20% and particularly preferably at least 30%. To achieve a sufficient mechanical stability of the membrane and also a sufficient capillary effect of the membrane, it is advantageous if the porous proportion of the area of the first surface is less than 70% and particularly advantageous if it is less than 60%. The proportion of pores in the second surface is generally lower than the porous proportion of the area of the first surface, and is at least approximately 5%, preferably at least 10%.

As was already explained, the membrane has approximately oval or circular openings in the first and second surfaces, which openings penetrate the first and second cover layers, respectively, and are connected to the supporting layer. The average diameter of the openings in the first surface thereby differs from the average diameter of the openings in the second surface by a factor of less than 2. At the same time, the openings in the surfaces appear smaller than the pores in the supporting layer. The average diameter of the openings in the second surface is preferably 0.5 to 1.5 times as large as the average diameter of the openings in the first surface. It is advantageous if the average diameter of the openings in the second surface lies in the range from 2 to 20 µm. Unlike the microporous membranes of the prior art, the present membrane is thus essentially symmetrical on the surfaces with respect to the pore sizes.

The cover layers, formed integrally with the supporting layer on the first surface and the second surface of the membrane, have pores that are on average smaller than the pores in the supporting layer. As a consequence, the cover layers also provide a contribution to the through-flow resistance during the passage of a liquid through the membrane. In view of a specific separation task, i.e. the separation of components of a specific size from a liquid, the smallest pores of the membrane (separating pores) are thus located in the cover layers or within the cover layer that has the smaller pores.

With a view to applications in which the tasks of the membrane involve filtration, the present membranes have in a preferred embodiment a diameter $d_{max}$, determined by means of the bubble point method, of the maximum separating pore in the range from 2 to 20 μm and particularly preferably in the range from 5 to 10 μm.

In a further preferred embodiment of the present membrane, the diameter of the pores in the supporting layer, starting from the first cover layer in the direction of the second cover layer, is essentially constant in a first area of the supporting layer over at least 50% of the thickness of the supporting layer. The first area of the supporting layer thus presents, in respect of the pore structure, an essentially isotropic area. Within the context of the present invention, an essentially isotropic area is thereby understood as an area of the membrane wall having essentially constant pore size, wherein an assessment is carried out using scanning electron microscopic or transmission electron microscopic images. The isotropic area can also be considered as an area with flow channels having an essentially constant average diameter and extending through the membrane wall. As in every membrane, the actual pore size also varies somewhat in the membrane according to the invention, i.e. the pore size has a certain distribution, even if the pore size distribution appears visually isotropic. Therefore, embodiments of the invention also comprise essentially isotropic areas in which the pore size changes by a maximum of approximately 15-20%.

In a preferred embodiment, in a second area of the supporting layer facing the second cover layer, the diameter of the pores can be consistently larger than in the first area. In a further preferred embodiment, the pore diameter in a second area of the supporting layer adjacent to the first area initially increases in a direction toward the second cover layer, passes through a maximum, and then decreases in the direction of the second cover layer to the pore diameter present in the second cover layer. At the same time, the proportions of pores in the structure in the supporting layer and in particular in the second cover layer are different from each other, as already results from the porous proportion of the area of the second cover layer in comparison with the total porosity of the membrane.

The present membranes are especially suitable for applications in medical technology, e.g. as filter elements in drip chambers for infusion sets for the administration of infusion solutions. In applications of this type, the membrane enables that the flow of the infusion solutions, such as aqueous sodium chloride, glucose, and lipid solutions, remains constant, independent of the hydrostatic pressure head occurring thereby, and that at the same time a fluid column remains in the infusion tube at the end of the administration. The skin covering the cover layers and the branches of the present membrane thereby exerts a positive effect in the direction of a low adsorption of components of the infusion solutions, such as lipids, amino acids, carbohydrates, lactates, etc., due to the smooth, even structure thereof. The membrane according to the invention thereby is located as a filter element in the area of the outlet of the drip chamber in the infusion tube connected to the drip chamber of the infusion set.

The invention therefore also relates to an infusion set for administering infusion solutions, comprising a drip chamber and an infusion tube connected to the drip chamber, in which the membrane according to the invention is inserted in the infusion tube in the area of the outlet of the drip chamber.

The present membranes can be produced by a method using phase separation induced by a non-solvent. A method of this type for producing the membrane according to the invention comprises the steps:

a. Preparation of a homogeneous casting solution of a polymer component, comprising a hydrophobic first polymer from the group of aromatic sulfone polymers and a hydrophilic second polymer, and possibly a hydrophilic third polymer, in a solvent system, wherein the casting solution comprises 10 to 25 wt. %, preferably 12 to 18 wt. %, relative to the weight of the solution, of the hydrophobic first polymer, 2 to 20 wt. %, preferably 5 to 18 wt. %, relative to the weight of the solution, of the hydrophilic second polymer, and the hydrophilic third polymer, if present, is in a concentration in the range from 0.2 to 20 wt. %, preferably 0.5 to 15 wt. %, relative to the weight of the casting solution, and the solvent system consists of 5 to 80 wt. %, preferably 10 to 60 wt. %, relative to the weight of the solution, of a solvent for the polymer component, 0 to 80 wt. %, preferably 5 to 60 wt. %, relative to the weight of the solution, of a latent solvent for the polymer component, as well as 0 to 70 wt. %, preferably 0 to 40 wt. %, relative to the weight of the solution, of a non-solvent for the polymer component,
b. Conditioning the homogeneous casting solution to a molding temperature,
c. Pouring the homogeneous casting solution onto a thermally conditionable carrier to form a film,
d. Conveying of the film located on the carrier through a climate-controlled zone,
e. Introduction of the film located on the carrier into a coagulation liquid and inducing the coagulation of the film to form a membrane structure,
f. Drawing off the membrane structure from the carrier by means of a withdrawal device within the coagulation liquid,
g. Stabilizing the membrane structure in the coagulation medium,
h. Extracting the membrane thus obtained and subsequent drying of the membrane,
wherein the casting solution is determined via selection and concentration of the components contained therein such that it has a viscosity of at least 8 Pa s at a temperature of 40° C., and the individual method conditions are to be set such that the membrane according to the invention with the properties defined in claim 1 is obtained.

The previously listed polymers are to be used as the hydrophobic first polymer from the group consisting of aromatic sulfone polymers, on which polymer the membrane according to the invention is based. The same applies for the hydrophilic second polymer and for the hydrophilic third polymer, if applicable. The solvent system used to produce the casting solution is adjusted to the membrane-forming sulfone polymer. The solvent system preferably comprises polar aprotic solvents, such as dimethylformamide, dimethylacetamide, dimethyl sulfoxide, N-methylpyrrolidone, or mixtures thereof, or protic solvents such as ε-caprolactam. In addition, the solvent system can contain up to 80 wt. % of a latent solvent, wherein a latent solvent is understood in the context of the present invention as one that dissolves the sulfone polymer only poorly or only at increased temperature. In case of the preferred use of ε-caprolactam as a solvent, for example γ-butyrolactone, propylene carbonate, or polyalkylene glycol can be used. In addition, the solvent system can contain non-solvents for the membrane forming polymers, such as water, glycerine, low-molecular-weight polyethylene glycols with a weighted-average molecular weight of less than 1000 daltons, or low-molecular-weight alcohols such as ethanol or isopropyl alcohol.

It is important for implementing the method for producing the membrane according to the invention that the viscosity of the casting solution is set to a value above 8 Pa s, and advantageous if the viscosity is set to a value above 10 Pa s, wherein the viscosity is determined at 60° C. Adjusting the viscosity can take place in particular using the concentration of the hydrophilic second polymer used in the method according to the invention, wherein the type and molecular weight of the hydrophilic second polymer are also influential. Otherwise, the solvent system used also affects the viscosity of the casting solution, thus e.g. the type or proportion of solvent, latent solvent, and non-solvent. For example, when using ε-caprolactam as the solvent, primarily also in combination with γ-butyrolactone, propylene carbonate, or polyalkylene glycol as the latent solvent, viscosities can be realized in the required range.

It was found in tests that the viscosity of the casting solution, together with the thickness of the membrane to be produced, has a decisive influence on the structure of the membrane, which should be understood in particular as the manifestation of the three-dimensional network structure and the surfaces with the pores or openings located therein. The high viscosity of the casting solutions, in conjunction with the range required according to the invention with respect to the thickness of the membrane, has shown itself to be important for the formation of a three-dimensional network structure with thick branches and an essentially symmetric structure across the wall thickness, in which the average diameters of the openings in the surfaces differ by a factor of less than 2, and in which in a preferred case the diameter of the pores, starting from the first cover layer in the direction of the second cover layer, is essentially constant in a first area of the supporting layer over at least 50% of the thickness of the supporting layer.

Membranes from solutions with lower viscosities below 8 Pa s and with higher membrane thicknesses have a pronounced asymmetric structure across the membrane wall with significant differences with regard to the average diameters of the openings in the two membrane surfaces, which then differ by a factor of more than 2.

The pouring of the casting solution to form a film can take place in a known way, for example by means of conventional molding tools like sheeting dies, casting molds, or doctor blades. The casting solution is set to the molding temperature at the latest in the molding tool. For the production of the membranes according to the invention, it has been demonstrated as favorable if the temperature of the casting solution supplied to the molding tool essentially corresponds to the temperature of the molding tool, and does not deviate therefrom by more than approximately 20° C., preferably by not more than 15° C. It has been thereby determined as advantageous if the molding tool has a temperature of at least 50° C.

Pouring the casting solution takes place onto a thermally conditionable carrier, wherein conventional carriers can also be used here, from which the coagulated membrane can be later drawn off. For example, coated papers or metal tapes can be used. The thermally conditionable carrier is preferably a thermally conditionable heating roller, i.e. a casting roller onto which the film is poured. The temperature of the thermally conditionable carrier is set preferably to a value that deviates by at most approximately ±20% from the molding temperature of the casting solution. This is advantageous for maintaining the viscosity of the casting solution in the required range, and also for guaranteeing a sufficient open-pored structure in the resulting membrane.

It is further necessary, in order to generate the virtually symmetric structure, to guide the film located on the carrier through a climate-controlled zone in which a defined temperature and a defined relative humidity are set. The temperature in the climate-controlled zone preferably lies in the range between 40 and 60° C., and particularly preferably in the range between 45 and 55° C. The relative humidity is preferably set to values in the range from 40 to 75%. The residence time of the film in the climate-controlled zone as well as the overflow speed of the air over the poured film in the climate-controlled zone are to be assessed such that a pre-coagulation is induced by uptake of the atmospheric humidity, functioning as a non-solvent, on the side of the casting solution facing away from the thermally conditionable carrier, i.e. on the air side.

The air side is later the second surface of the filtration membrane according to the invention. The residence time of the film in the climate-controlled zone is preferably greater than 10 s and particularly preferably greater than 15 s.

After passing through the climate-controlled zone, the film located on the carrier is fed into a coagulation liquid and coagulation is induced to form the membrane structure. In this case, to achieve the membrane structure according to the invention, the coagulation liquid is conditioned to a temperature that is 0 to 60° C. lower than the temperature of the thermally-conditionable carrier. To produce membranes according to the invention with high transmembrane flow, the coagulation liquid is preferably conditioned to a temperature that is 20 to 60° C. lower than the temperature of the thermally conditionable carrier, and particularly preferably conditioned to a temperature that is 35 to 60° C. lower than the temperature of the thermally conditionable carrier. In an advantageous embodiment of the method according to the invention, the coagulation liquid is water or a water bath. The residence time of the film in the coagulation liquid preferably is on the same order of magnitude as in the climate-controlled zone and thus greater than 10 s and particularly preferably greater than 15 s.

The film is initially precipitated in the coagulation liquid to the extent that the structure already has a sufficient stability and can be drawn off of the carrier, i.e. preferably from the casting roller. Following the withdrawal device, the coagulation is completed and the membrane stabilized in subsequent coagulation baths. These coagulation baths can have a higher temperature in comparison to the first, previously described coagulation bath. The temperature can also be increased step-wise from bath to bath. An extraction of the solvent system and generally of parts of the hydrophilic second polymer from the membrane thereby takes place at the same time in the coagulation baths, such that the coagulation baths simultaneously function as wash baths or extraction baths. Water is preferably used as the coagulation or wash medium in these coagulation or wash baths.

After the extraction, the membrane obtained is dried for example by means of a drum dryer and the dry membrane is then wound up. During the extraction and drying of the membrane, a slight drawing is advantageous to definitively set certain membrane properties such as the surface porosity and the separation properties.

The invention will be subsequently explained in more detail on the basis of the following examples and figures, wherein the scope of the invention is not limited by the examples.

The content of the figures is as follows:

FIG. 1: Scanning electron microscopic (SEM) image of a cross section of the membrane according to Example 1 at 250 times magnification.

FIG. 2: SEM image of a portion of the cross section of the membrane according to Example 1 in the area of the membrane side which was facing the casting roller during production (roller side), at 2000 times magnification.

FIG. 3: SEM image of the surface of the membrane according to Example 1, which surface was facing the casting roller during production (roller side), at 100 times magnification.

FIG. 4: SEM image of the surface of the membrane according to Example 1, which surface was facing away from the casting roller during production (air side), at 100 times magnification.

Figure 5:
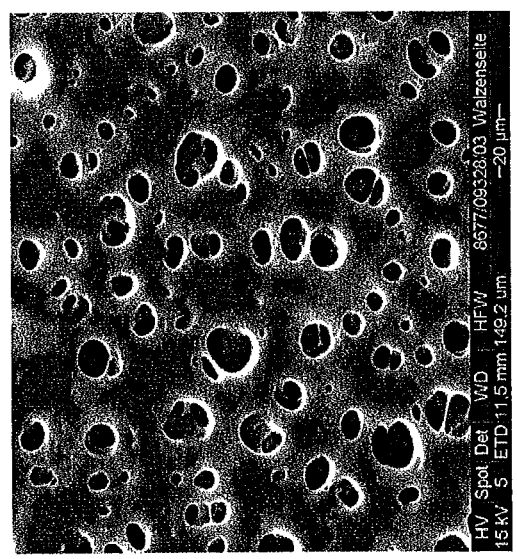

FIG. 5: SEM image of the surface of the membrane according to Example 1, which surface was facing the casting roller during production (roller side), at 500 times magnification.

FIG. 6: SEM image of the surface of the membrane according to Example 1, which surface was facing away from the casting roller during production (air side), at 500 times magnification.

Figure 7:
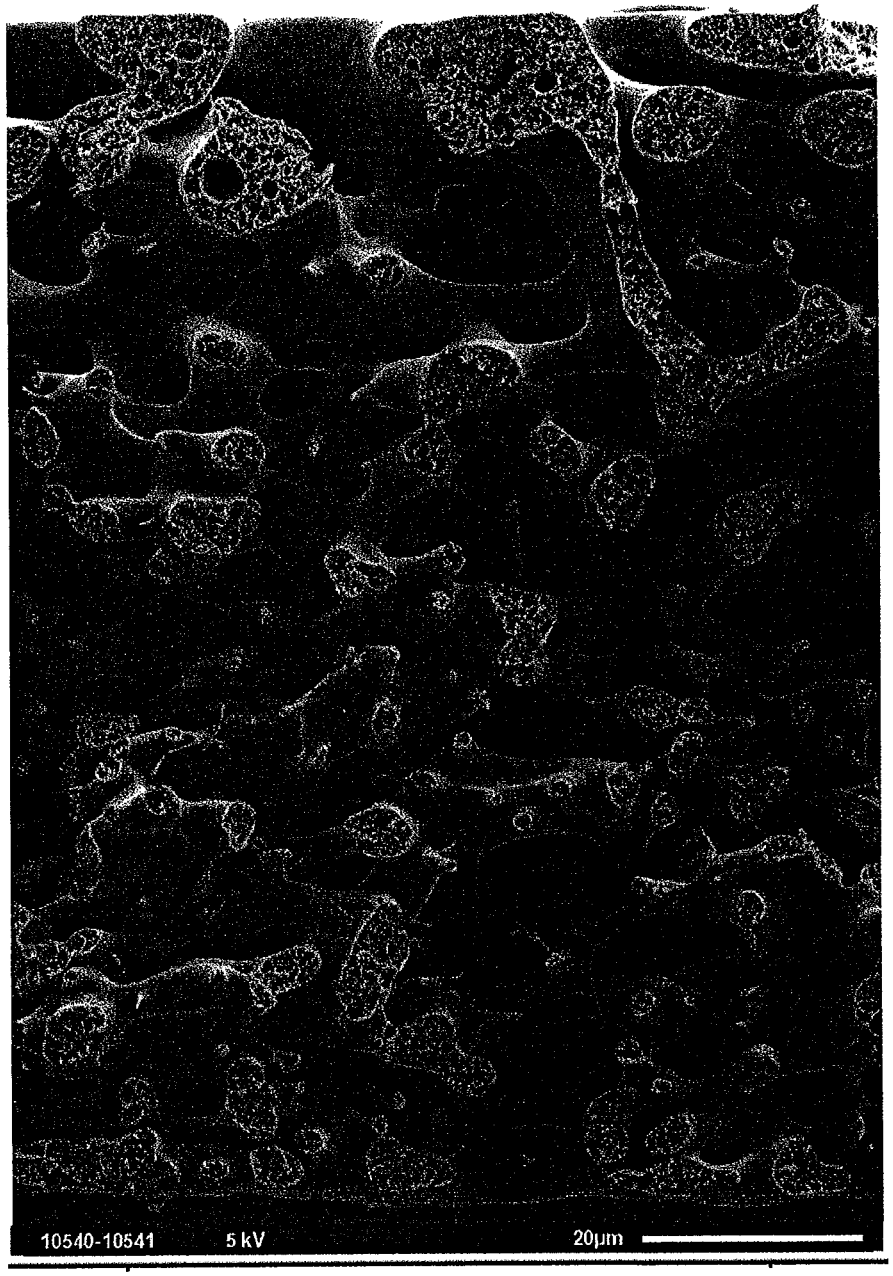

FIG. 7: SEM image of the entire cross section of the membrane according to Example 1 at approximately 1600 times magnification.

Figure 8:
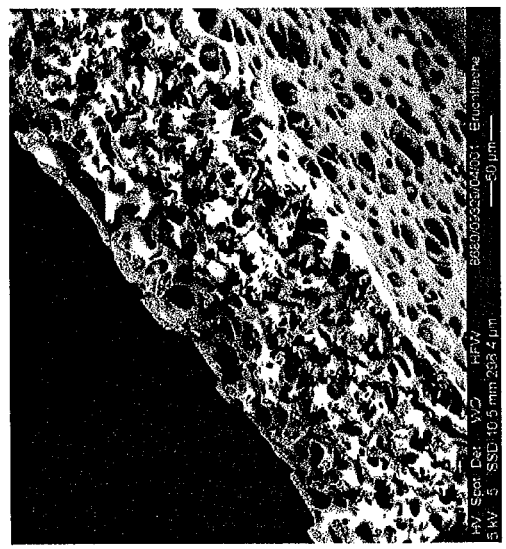

FIG. 8: SEM image of a cross section of the membrane according to Example 2 at 250 times magnification.

Figure 9:
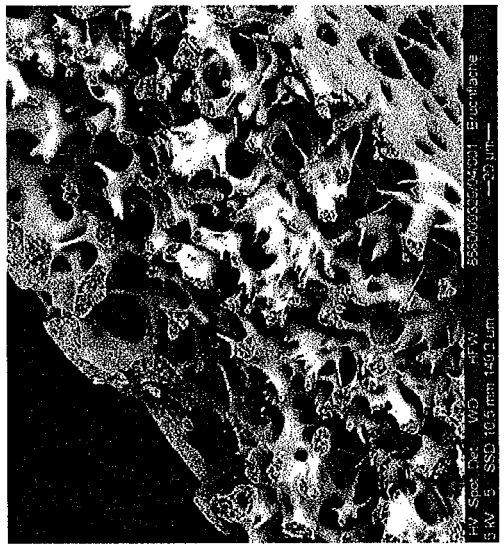

FIG. 9: SEM image of the cross section of the membrane according to Example 2 in the area of the membrane side at 500 times magnification.

Figure 10:
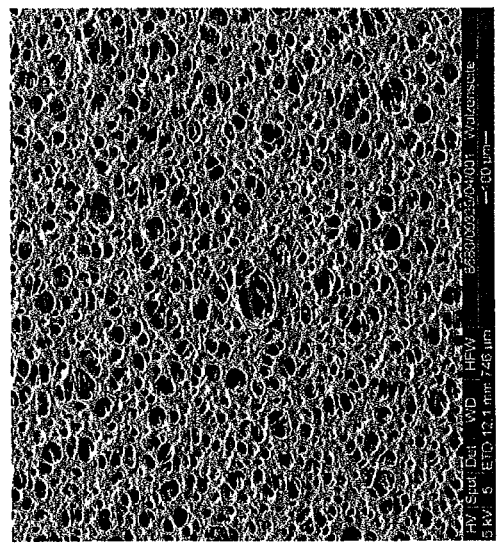

FIG. 10: SEM image of the surface of the membrane according to Example 2, which surface was facing the casting roller during production (roller side), at 100 times magnification.

Figure 11:
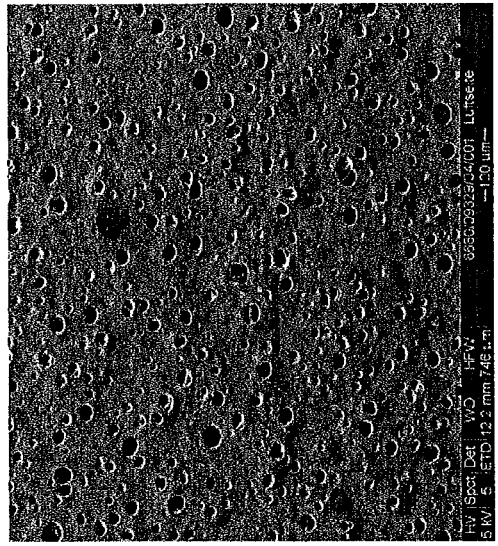

FIG. 11: SEM image of the surface of the membrane according to Example 2, which surface was facing away from the casting roller during production (air side), at 100 times magnification.

Figure 12:
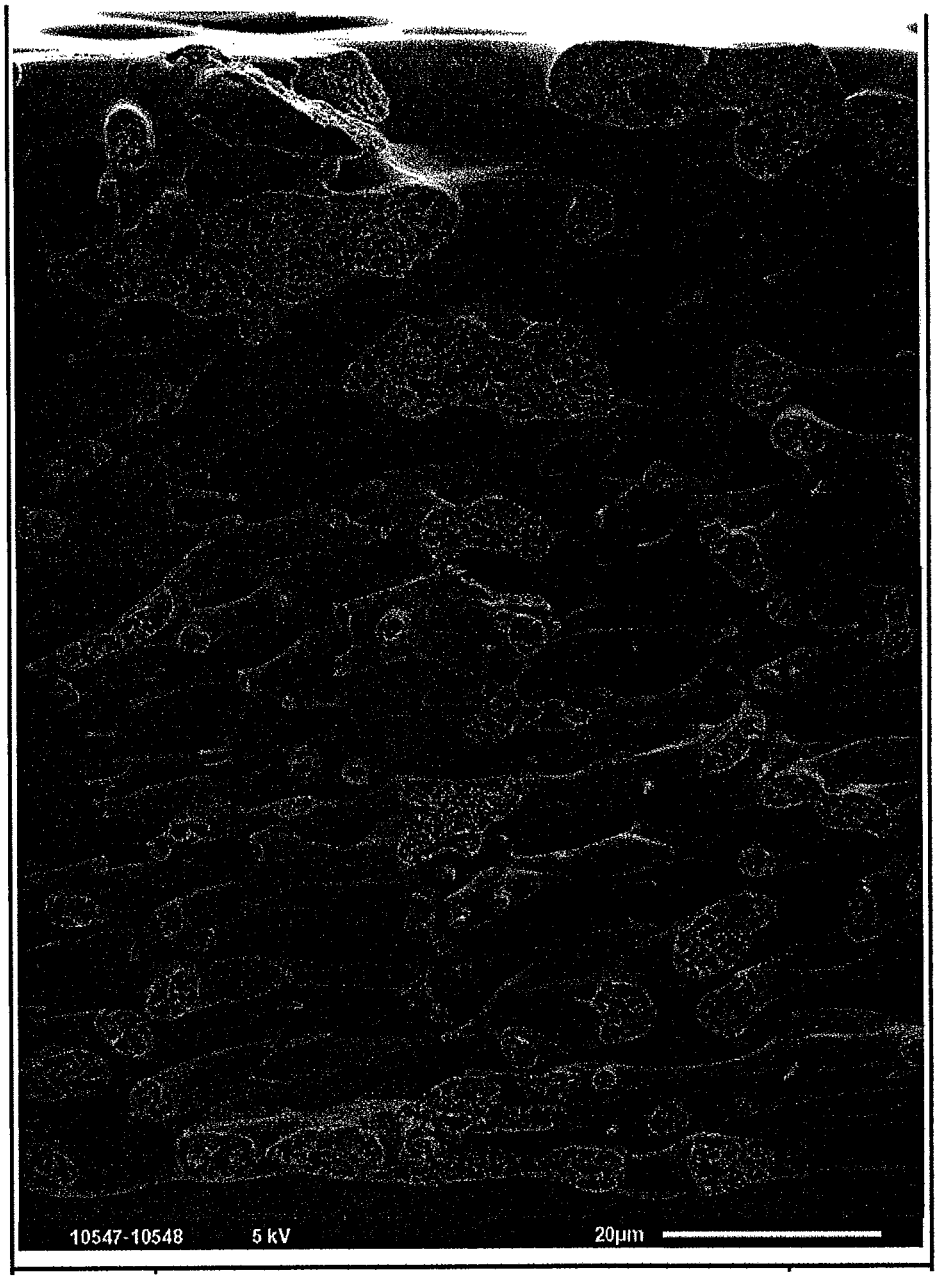

FIG. 12: SEM image of the entire cross section of the membrane according to Example 2 at approximately 1600 times magnification.

Figure 13:
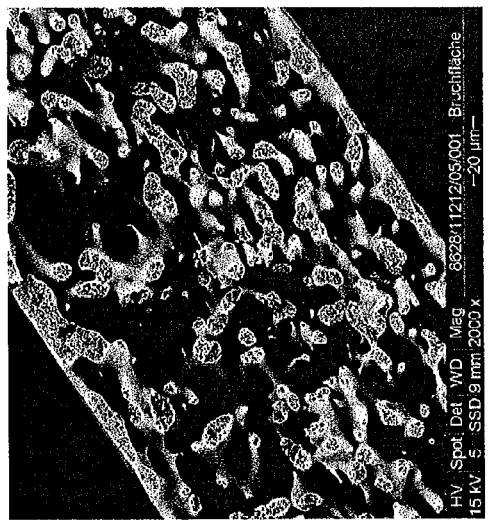

FIG. 13: SEM image of a cross section of the membrane according to Example 3 at 250 times magnification.

Figure 14:
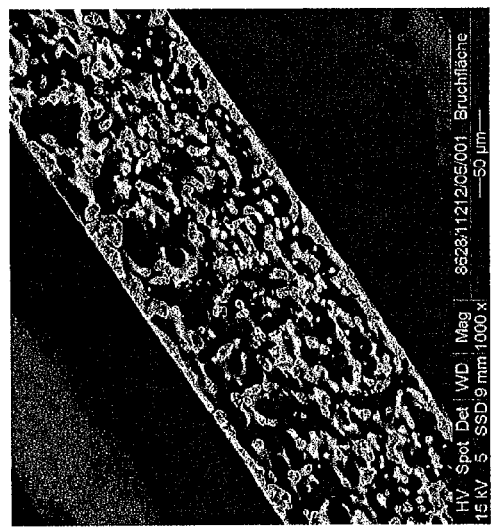

FIG. 14: SEM image of the cross section of the membrane according to Example 3 in the area of the membrane side, at 500 times magnification.

Figure 15:
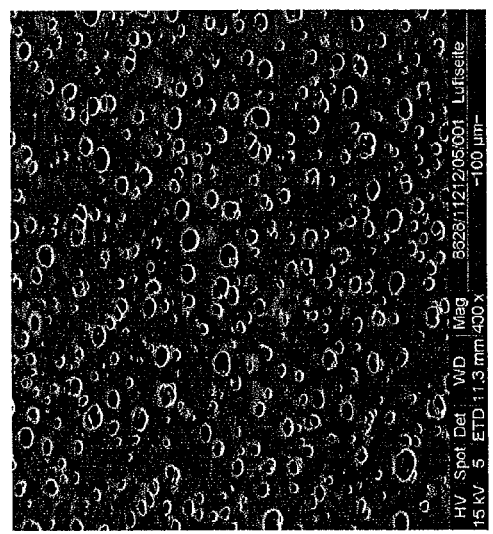

FIG. 15: SEM image of the surface of the membrane according to Example 3, which surface was facing the casting roller during production (roller side), at 100 times magnification.

Figure 16:
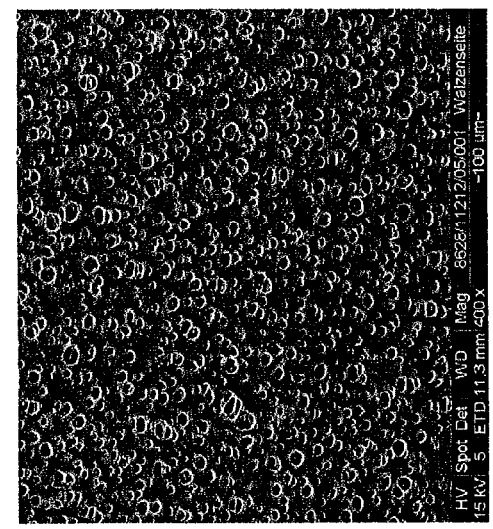

FIG. 16: SEM image of the surface of the membrane according to Example 3, which surface was facing away from the casting roller during production (air side), at 100 times magnification.

Figure 17:
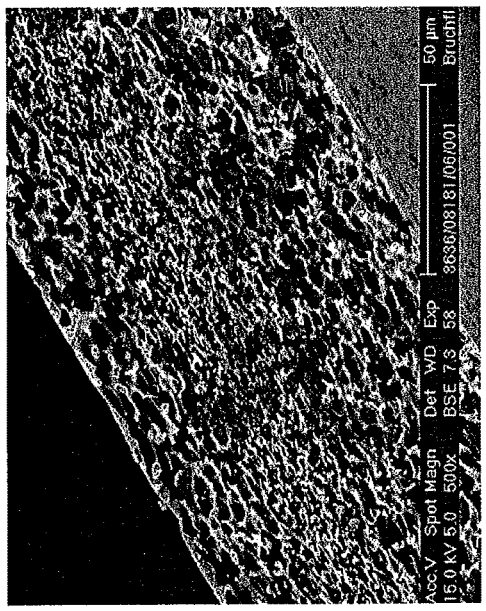

FIG. 17: SEM image of a cross section of the membrane according to Comparative Example 1.

Figure 18:
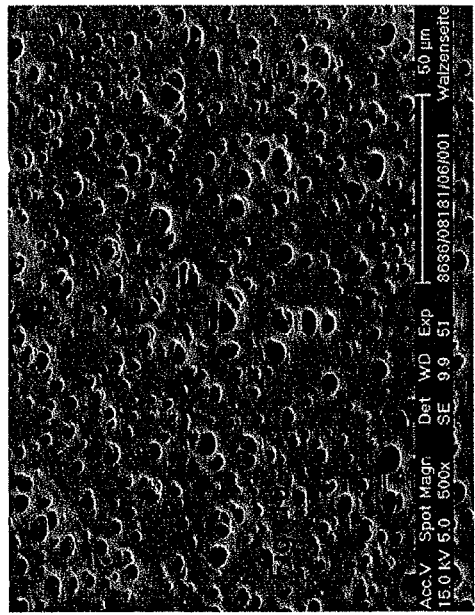

FIG. 18: SEM image of the surface of the membrane according to Comparative Example 1, which surface was facing the roller during production (roller side).

Figure 19:
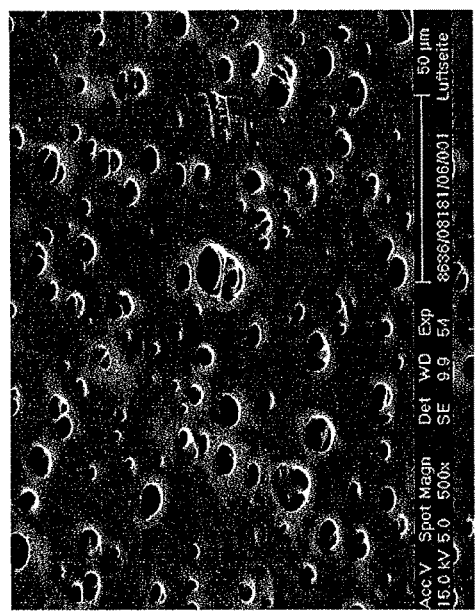

FIG. 19: SEM image of the surface of the membrane according to Comparative Example 1, which surface was facing away from the roller during production (air side).

Figure 20:
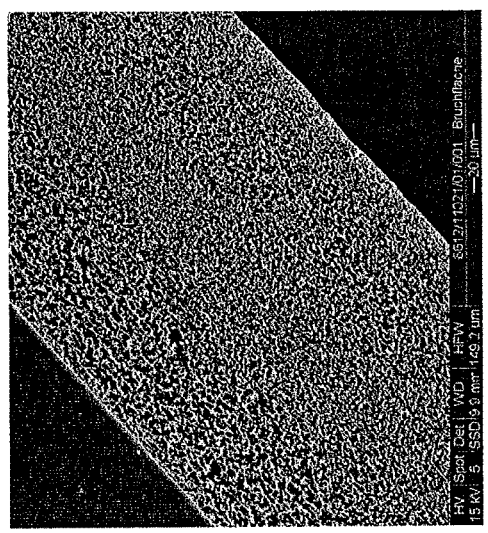

FIG. 20: SEM image of a cross section of the membrane according to Comparative Example 2.

Figure 21:
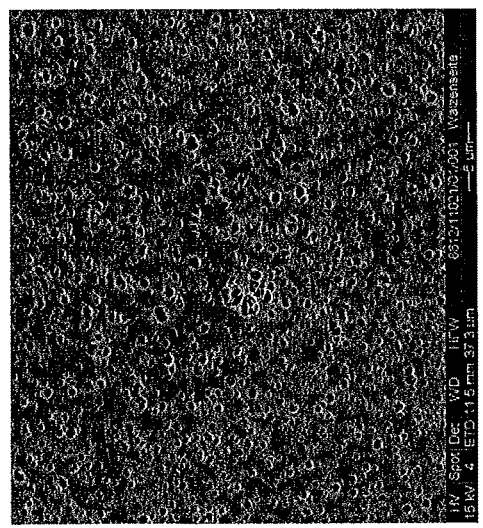

FIG. 21: SEM image of the surface of the membrane according to Comparative Example 2, which surface was facing the roller during production (roller side).

Figure 22:
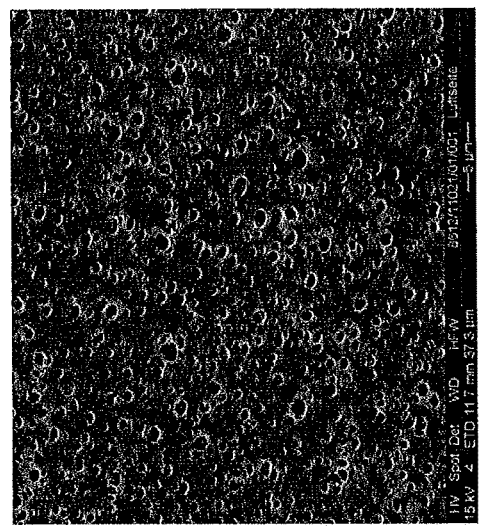

FIG. 22: SEM image of the surface of the membrane according to Comparative Example 2, which surface was facing away from the roller during production (air side).

Figure 23:
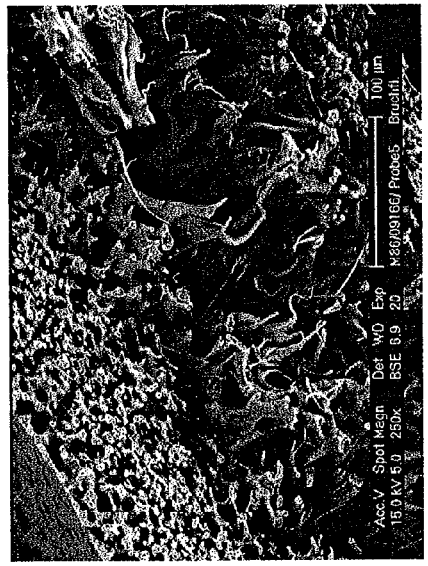

FIG. 23: SEM image of a cross section of the membrane according to Comparative Example 3b at 100 times magnification.

Figure 24:
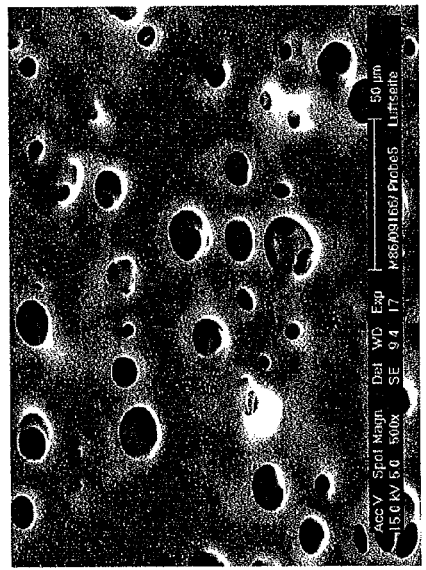

FIG. 24: SEM image of the cross section of the membrane according to Comparative Example 3b at 250 times magnification.

Figure 25:
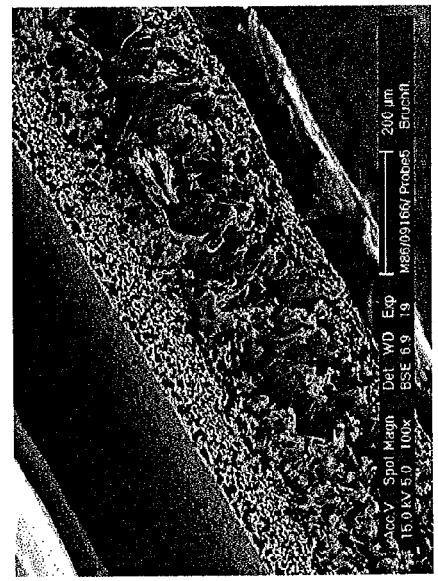

FIG. 25: SEM image of the surface of the membrane according to Comparative Example 3b, which surface was facing the roller during production (roller side), at 500 times magnification.

Figure 26:
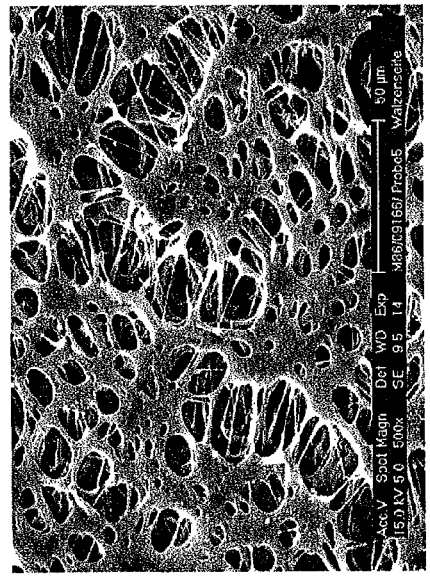

FIG. 26: SEM image of the surface of the membrane according to Comparative Example 3b, which surface was facing away from the roller during production (air side), at 500 times magnification.

Figure 27:
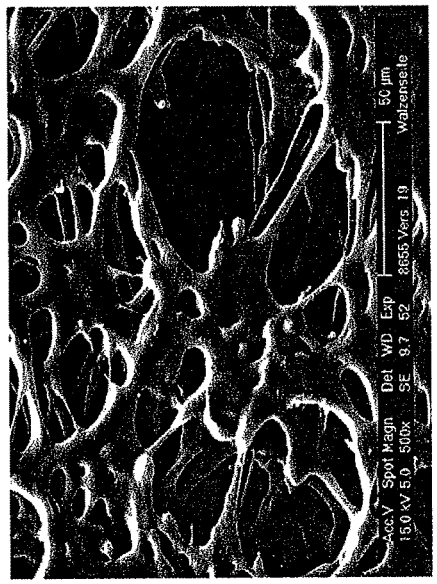

FIG. 27: SEM image of a cross section of the membrane according to Comparative Example 4.

Figure 28:
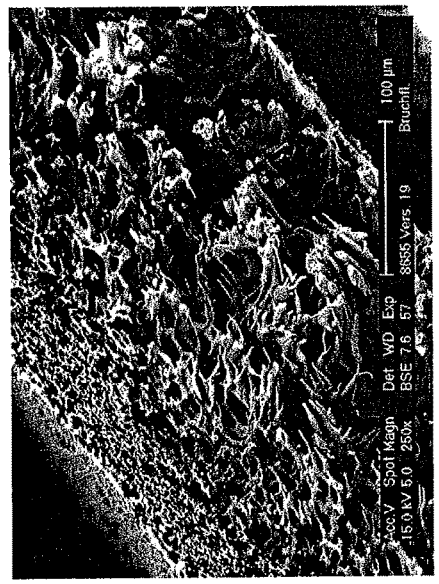

FIG. 28: SEM image of the surface of the membrane according to Comparative Example 4, which surface was facing the roller during production (roller side).

Figure 29:
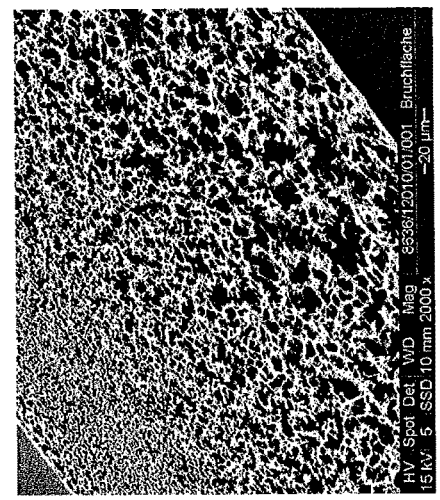

FIG. 29: SEM image of the surface of the membrane according to Comparative Example 4, which surface was facing away from the roller during production (air side).

Figure 30:
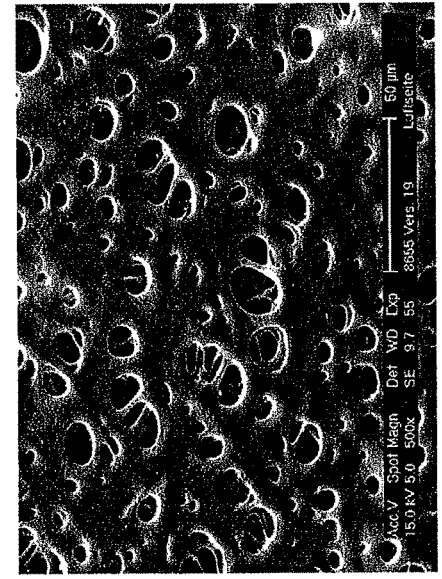

FIG. 30: SEM image of a cross section of the membrane according to Comparative Example 6.

The following methods are used for characterizing the membranes:

Determination of the Viscosity of the Casting Solution:

The viscosity of the casting solution is determined at a temperature of 60° C. by means of a rotational rheometer (RheoStress 1, Haake) using a Z20 DIN cylinder sensor device. The measurement takes place at a shear rate of 10 $s^{-1}$.

Determination of Volume Porosity

Four samples of approximately 15 $cm^2$ of the membrane to be tested are weighed out and placed in approximately 50 ml water for 16 h. The samples are subsequently removed from the water and the excess water is removed by means of blotting paper. The samples thus pretreated are weighed to determine the wet weight and afterwards dried at 50° C. for 16 h. After cooling, the weight of the dry samples is determined (dry weight).

The volume porosity is determined from the average value of the water uptake (wet weight minus dry weight) relative to the average value of the dry weight of the samples, using the densities for water and for the polymer (hydrophobic first polymer) forming the membrane.

Determination of the Transmembrane Flow (Water Permeability):

Disc-shaped membrane samples are stamped out of the membrane to be tested and then clamped fluid-tight at the perimeter in a suitable sample holder such that a free measuring area of 17.35 $cm^2$ results. The sample holder is located in a housing that can be penetrated under pressure by water. The clamped membrane sample is then penetrated, from the side on which the surface of the membrane with the smaller pores is located, by deionized water conditioned to 25° C. at a defined pressure between 0.1 and 0.2 bar. The water volume that flows through the membrane sample during a measuring period of 60 s is determined gravimetrically or volumetrically.

The transmembrane flow, TMF, is determined according to formula (III)

$$TMF\left[\frac{1}{m^2 \cdot h \cdot \text{bar}}\right] = \frac{V_w}{\Delta t \cdot A_M \cdot \Delta p} \cdot 600 \qquad \text{III}$$

where:
Vw=volume of water [ml] flowing through the membrane sample during the measuring period
Δt=measuring time [min]
$A_M$=area of the membrane sample penetrated (17.35 cm²)
Δp=pressure set during the measurement [bar]
Determination of the Maximum Separating Pore:

The diameter of the maximum separating pore is determined by means of the bubble point method (ASTM No. 128-61 and F 316-86), where for example the method described in DE-A-36 17 724 is suitable. Thereby, $d_{max}$ results from the vapor pressure $P_B$ associated with the bubble point according to the equation $$d_{max} = \sigma_B / P_B$$

where $\sigma_B$ is a constant that is primarily dependent on the wetting liquid used during the measurement. For water, $\sigma_B$ is 2.07 μm·bar at 25° C.
Determination of Breaking Force and Tensile Strength:

Measuring the breaking force of the membrane takes place using a standard, universal testing machine from Zwick (Ulm, Germany). For this purpose, samples are cut from the flat membrane to be tested, the edges thereof oriented in the production direction and transverse to the production direction. The samples have a width of 15 mm and are clamped in the testing machine such that a free length of 25 cm results.

The membrane samples are stretched at constant speed in the longitudinal direction or in the transverse direction of the samples until rupture. The force required for this is measured as a function of the change in length and retained in a force/elongation diagram. The measurement takes place as multiple determinations on five membrane samples at 100 mm clamping length and at a traction speed of 500 mm/min. The pretension weight is 2.5 cN. The force required to break, BK, is determined as the average numeric value in cN and the elongation at break achieved thereby as a % of the original length.

The tensile strength $\sigma_B$ of the membrane sample in cN/mm² is obtained by standardizing the breaking force BK to the cross-sectional area $A_Q$ of the membrane wall, which results from the sample width and the membrane thickness.
Examination of the Fluid Column Maintained by the Membrane:

A sample with a diameter of approximately 1.8 cm is stamped out of the membrane to be tested. The sample is embedded in a sample holder fluid-tight at the outer edge thereof such that a free area with a diameter of 1.2 cm (1.13 cm² measurement area) results in the center. The sample holder is provided with an inlet port at the upper end thereof and with an outlet port at the lower end thereof. The upper end of a flexible tube having an inside diameter of 3 mm and a length of approximately 1.75 m is connected to the outlet port. The lower end of the tube is positioned at a height of 1 m below the membrane sample and discharges openly into a collection container. The inlet port is connected to a water container that contains approximately 1 l.

The flexible tube is clamped off by means of a roller clamp and the water container above the sample holder is filled with water. At the beginning of the test, the roller clamp is opened and the water flow through the membrane sample and the tube is started. After passage of the entire amount of water provided, it is tested whether a fluid column of 1 m in height is maintained by the membrane sample in the tube beneath the membrane.

EXAMPLE 1

33 kg γ-butyrolactone, 33 kg ε-caprolactam, 4.2 kg glycerine, and 0.8 kg water were placed as a solvent system in a heatable vessel and mixed into a homogeneous liquid. 1.3 kg sulfonated polyethersulfone (SPES) with a degree of sulfonation of 5% was dissolved within 1 h in this solvent system while stirring, and then 15.22 kg polyethersulfone (PES, Ultrason E6020, BASF) was sprinkled in while stirring and dissolved over 4 h. Afterwards, 12.50 kg polyvinylpyrrolidone (PVP, K30, ISP), was stirred in, finely distributed, and homogenized. By applying vacuum and purging with nitrogen, the oxygen was largely removed from the vessel. Afterwards, the vessel was heated to 80° C. and a homogeneous casting solution was produced within 36 h under intensive stirring. Afterwards, the casting solution was cooled to 70° C. and degassed by means of vacuum. The solution obtained had a viscosity of 11.6 Pa s at 40° C.

The finished casting solution was poured by means of a casting mold conditioned to 80° C. onto a metal casting roller conditioned to 65° C. to form a film with a thickness of approximately 130 μm. The film, located on the casting roller, was fed through a climate-controlled zone and for approximately 26 s impinged with a climate of 50° C. and 63% relative humidity (dew point approximately 40° C.) before said film was fed into a coagulation bath filled with water conditioned to 65° C. After a residence time of 26 s to form the membrane structure, the film was drawn off from the casting roller by means of a drawing off roller. In subsequent wash baths, the membrane was fixed in water increasing in temperature step-wise to 90° C. and the solvent together with a large part of the PVP was extracted. The drying of the membrane took place by means of a drum dryer.

The membrane thus produced was permanently hydrophilic, spontaneously wettable with water, and had a thickness of approximately 95 μm and a maximum separating pore of 6.9 μm as determined by means of the bubble point method. It had a transmembrane flow of approximately 1320 ml/(cm²·min·bar) and a porosity of approximately 81 vol. %. An average tensile strength of 770 cN/mm² in the longitudinal direction (production direction) and 760 cN/mm² in the transverse direction was measured for the membrane. The average elongation at break was 28% in the longitudinal direction and 47% in the transverse direction. The membrane maintained a fluid column of at least one meter without any problems in the test.

FIG. 1 shows a cross section of the membrane from Example 1, in which on the surfaces of the membrane on the roller side (right side in the SEM image shown in FIG. 1) and also on the air side (left side in the SEM image shown in FIG. 1), a cover layer having pores can be recognized. A coarse-pored supporting layer extends between the cover layers, wherein the cover layer facing the roller side adjoins a first area of the supporting layer, in which first area the pore size is essentially constant and which first area, starting from the roller side, extends over approximately 70% of the supporting layer. In a second area of the supporting layer, which second area extends to the cover layer corresponding to the air side, the pore structure appears more coarsely pored than in the first area of the supporting layer.

In FIG. 2, which shows a portion of the membrane cross section in the area of the membrane side that was facing away from the casting roller during production of the membrane (air side) at 2000 times magnification, it can be recognized that the membrane structure of the cover layer and also the branches of the supporting structure have a skin on the outer side and a porous structure in the interior, wherein the skin of the cover layers and also of the branches in the supporting layer appears smooth, uniform, and even, as determined by means of scanning electron microscopy. The latter is illustrated by means of sections of the membrane surface on the roller side and on the air side at 500 times magnification in FIG. 5 and FIG. 6.

The membrane of Example 1 had a structure across the thickness thereof, as is depicted in the SEM image of FIG. 7. At the magnification of approximately 1600 times shown here, it is clearly recognizable that the predominant majority of the branches forming the structure have a diameter of more than 0.5 µm at their respectively thinnest point. From FIGS. 3 to 6, it is also clear that the openings or pores in the surfaces of the membrane from Example 1 have an island-sea structure, in which on average approximately oval or circular openings are surrounded by the cover layer in the surfaces, the cover layers thus respectively forming the continuous phase in the form of webs surrounding the openings or pores, which phase surrounds the openings.

EXAMPLE 2

The procedure was the same as in Example 1, except that a coagulation bath temperature of 20° C. was set.

The membrane had a thickness of approximately 100 µm and was likewise permanently hydrophilic and spontaneously wettable with water. It had a maximum separating pore of 8.3 µm, determined by means of the bubble point method, a transmembrane flow of approximately 2080 ml/(cm$^2$·min·bar) and a porosity of approximately 83 vol. %. The membrane had an average tensile strength of 740 cN/mm$^2$ in the longitudinal direction (production direction) and 730 cN/mm$^2$ in the transverse direction. The average elongation at break was 25% in the longitudinal direction and 43% in the transverse direction. The average diameter of the pores in the surface that was facing the casting roller during casting of the film (roller side) was 10.5 µm, and that of the pores in the surface that was initially facing the air during casting of the film (air side) was 8.2 µm. The proportion of pores in the surface on the roller side was 36.2% and on the air side was 6.8%, determined using image analysis methods. The membrane maintained a fluid column of at least one meter without any problems in the test.

The membrane structure resembles that of the membrane from Example 1. By means of FIGS. 8 and 9, which show a cross section of the membrane from Example 2 in 250 times and 500 times magnification, respectively, cover layers can be recognized on both surfaces of the membrane. The supporting layer lying therebetween has a first area extending from the roller side (right side in the SEM image shown in FIGS. 8 and 9) with an essentially isotropic pore structure, which area extends across approximately 70% of the supporting layer. The pore structure in a second area of the supporting layer, which second area extends from the first area of the supporting layer in the direction of the air side of the membrane, appears more coarsely pored than in the first area.

It can also be clearly recognized by means of FIGS. 8 and 9 that the cover layers and the branches have an internal porous structure and a smooth, even skin on the outer side thereof. FIGS. 10 and 11 depict scanning electron microscopic images of the surfaces of the membrane from Example 2 (FIG. 10: roller side; FIG. 11: air side). These surfaces also have a clear island-sea structure, in which the approximately oval or circular openings in the surfaces are surrounded by the cover layer. FIG. 12 shows an SEM image, in approximately 1600 times magnification, of the cross section of the membrane from Example 2. It can be clearly recognized that practically all of the branches or webs have a diameter of at least 0.5 µm at the thinnest point thereof.

EXAMPLE 3

The casting solution from Example 1 was used. The casting solution was poured by means of a casting mold conditioned to 67° C. onto a metal casting roller conditioned to 66° C. to form a film with a thickness of approximately 140 µm. The film located on the casting roller was fed through a climate-controlled zone and for approximately 16 s impinged with a climate of 59° C. and 72% relative humidity (dew point approximately 45° C.) before said film was fed into a coagulation bath filled with water conditioned to 20° C. After a residence time of 16 s to form the membrane structure, the film was drawn off from the casting roller by means of a drawing off roller. In subsequent wash baths, the membrane was fixed in water increasing in temperature step-wise to 90° C. and the solvent, together with a large part of the PVP, was extracted. The drying of the membrane took place by means of a drum dryer.

The membrane thus produced was permanently hydrophilic, spontaneously wettable with water, had a thickness of approximately 110 µm and a maximum separating pore of 9.0 µm, determined by means of the bubble point method. It had a transmembrane flow of approximately 2000 ml/(cm$^2$·min·bar) and a porosity of approximately 81 vol. %. A tensile strength of 720 cN/mm$^2$ in the longitudinal direction (production direction) and 700 cN/mm$^2$ in the transverse direction was measured for the membrane. The average elongation at break was 29% in the longitudinal direction and 44% in the transverse direction. The membrane maintained a fluid column of at least one meter without any problems in the test.

With regard to the structure thereof, i.e. also with regard to the branches forming the structure, the membrane from Example 3 resembled the membrane from Example 1 or Example 2. In the cross section, the membrane from Example 3 had recognizable cover layers on both surfaces based on SEM images. The supporting layer lying therebetween has, according to FIG. 13 and FIG. 14, a first area extending from the roller side (right side in the SEM images shown in FIGS. 13 and 14) with an essentially isotropic pore structure, which first area extends across approximately 60% of the supporting layer. The pore structure in a second area of the supporting layer, which second area extends from this first area of the supporting layer in the direction of the air side of the membrane, appears more coarsely pored than in the first isotropic area. FIGS. 15 and 16 depict scanning electron microscopic images of the surfaces of the membrane from Example 3 (FIG. 15: roller side; FIG. 16: air side). These surfaces also clearly have an island-sea structure, in which the approximately oval or circular openings in the surfaces are surrounded by the cover layer.

COMPARATIVE EXAMPLE 1

The procedure was the same as in Example 1. Departing from Example 1, the casting roller temperature was 60° C. and the coagulation bath temperature 55° C. In addition, the temperature in the climate-controlled zone was 36.5° C. and the relative humidity was approximately 95% (dew point approximately 33° C.). In addition, the method was carried out such that there was a residence time of approximately 18.5 s in the climate-controlled zone and in the coagulation bath, respectively.

The approximately 95 μm thick membrane thus produced had a comparably fine-pored, sponge-like pore structure with fine branches. The maximum separating pore was 2.4 μm, determined by means of the bubble point method. The membrane had a transmembrane flow of approximately 474 ml/($cm^2$·min·bar) and thus a transmembrane flow that was too low.

The membrane from Comparative Example 1 shows an asymmetric structure across the wall thickness as seen in the cross section depicted in FIG. 17. In the wall interior, close to the middle of the wall, there is an area with minimal pore size. Starting from this region with minimal pore size, the size of the pores increases towards both surfaces, i.e. an asymmetric area is located on both sides of the area with minimal pore size. FIGS. 18 and 19 depict the surfaces of the membrane from Comparative Example 1 (FIG. 18: roller side; FIG. 19: air side).

COMPARATIVE EXAMPLE 2

The procedure was the same as in Example 1. Departing from Example 1, the casting roller temperature and the coagulation bath temperature was 27° C. In addition, the temperature in the climate-controlled zone was 40° C. and the relative humidity was approximately 78% (dew point approximately 35° C.). In addition, the method was carried out such that there was a residence time of approximately 12.5 s in the climate-controlled zone and in the coagulation bath, respectively.

The membrane thus produced likewise had a fine-pored, sponge-like pore structure. The maximum separating pore was 0.5 μm, determined by means of the bubble point method. The membrane had a transmembrane flow of only approximately 30 ml/($cm^2$·min·bar), which was thus significantly too low.

The cross section of the membrane from Comparative Example 2 depicted in FIG. 20 shows an asymmetric pore structure across the wall thickness with a region with minimal pore size located in the wall interior near the middle of the wall. Starting from this area with minimal pore size, the size of the pores increases towards both surfaces, i.e. an asymmetric area is located on both sides of the area with minimal pore size. FIGS. 21 and 22 depict scanning electron microscopic images of the surfaces of the membrane from Comparative Example 2 (FIG. 21: roller side; FIG. 22: air side).

COMPARATIVE EXAMPLES 3A AND 3B

The procedure was the same as in Example 1. Departing from Example 1, the casting roller temperature and the coagulation bath temperature were 79° C. and 75° C., respectively. The temperature in the climate-controlled zone was set to 50° C. and the relative humidity to approximately 75% (dew point approximately 42° C.). In addition, the method was carried out such that there was a residence time of approximately 26 s in the climate-controlled zone and in the coagulation bath, respectively. In addition, departing from Example 1, a film with a thickness of approximately 370 μm (Comparative Example 3a) and approximately 420 μm (Comparative Example 3b) was poured onto the casting roller, from which membranes with a thickness of 300 μm and 350 μm, respectively, were obtained.

The properties of the membranes from Comparative Examples 3a and 3b are listed in Table 1.

TABLE 1

| Membrane of | Thickness μm | TMF ml/($cm^2$ · min · bar) | Maximum separating pore μm |
|---|---|---|---|
| Comparative Example 3a | 300 | 870 | 4.8 |
| Comparative Example 3b | 350 | 270 | 4.8 |

The cross section of the membrane from Comparative Example 3b depicted in FIGS. 23 and 24 shows across the wall thickness a clearly asymmetric pore structure with an fine-pored structure on the roller side (right side in the SEM images shown in FIG. 23 and FIG. 24), which pore structure transitions into a very open-pored structure in the wall interior. Towards the air side (left side in the SEM images shown in FIG. 23 and FIG. 24), the structure transitions into a fine-pored area extending across approximately 25% of the wall thickness.

FIGS. 25 and 26 depict scanning electron microscopic images of the surfaces of the membrane from Comparative Example 3b (FIG. 25: roller side; FIG. 26: air side). On the roller side, the membrane from Comparative Example 3b shows a partially network-like and fibrillar structure with predominantly thin, fibril-like delimitations between irregularly shaped pores.

COMPARATIVE EXAMPLE 4

According to the method of Example 1, a homogeneous solution was produced of 13.95 wt. % polyethersulfone (PES, Ultrason E6020, BASF), 1.04 wt. % sulfonated polyethersulfone (SPES) with a degree of sulfonation of 5%, and 11.25 wt. % polyvinylpyrrolidone (PVP, K30, ISP) in a solvent system having 41.48 wt. % γ-butyrolactone, 13.83 wt. % ε-caprolactam, and 18.45 wt. % polyethylene glycol PEG 200, each relative to the weight of the total solution. The final solution had a viscosity of 3.7 Pa s at a measuring temperature of 40° C.

The finished casting solution was poured by means of a casting mold conditioned to 45° C. onto a metal casting roller conditioned to 75° C. to form a film. The film located on the casting roller was fed through a climate-controlled zone and for approximately 26 s impinged with a climate of 50° C. and 74% relative humidity (dew point approximately 47° C.) before said film was fed into a coagulation bath filled with water conditioned to 69.5° C. After a residence time of 26 s to form the membrane structure, the film was drawn off from the casting roller by means of a drawing off roller. In subsequent wash baths, the membrane was fixed in water and the solvent together with a large part of the PVP was extracted. The drying of the membrane took place by means of a drum dryer.

A membrane with a thickness of approximately 280 µm was produced. The membrane had a maximum separating pore of 3.9 µm, determined by means of the bubble point method, and a transmembrane flow of approximately 1250 ml/(cm²·min·bar).

As proven by the SEM images of the membrane cross section and the surfaces according to FIGS. 27 to 29, the membrane from this Comparative Example 4 had a pronounced asymmetric structure extending across the entire membrane wall, wherein the diameters of the pores in the surfaces of the membrane differed on average by a factor of more than 2.

COMPARATIVE EXAMPLE 5

The procedure was the same as in Comparative Example 4. Departing from Comparative Example 4, a film was poured onto a casting roller conditioned to 85° C., which film, after passing through the climate-controlled zone, was fed into a coagulation bath conditioned to 73° C. to form the membrane structure.

A membrane with a thickness of approximately 340 µm was produced. The membrane had a maximum separating pore of 2.5 µm and a transmembrane flow of approximately 630 ml/(cm²·min·bar). The structure of the membrane from Comparative Example 5 resembled that of the membrane from Comparative Example 4.

COMPARATIVE EXAMPLE 6

According to the method of Example 1, a homogeneous solution was produced of 13.84 wt. % polyethersulfone (PES, Ultrason E6020, BASF), 1.04 wt. % sulfonated polyethersulfone (SPES) with a degree of sulfonation of 5%, and 11.16 wt. % polyvinylpyrrolidone (PVP, K30, ISP) in a solvent system having 41.15 wt. % γ-butyrolactone, 13.72 wt. % ε-caprolactam, 18.29 wt. % polyethylene glycol PEG 200, and 0.80 wt. % water, each relative to the weight of the total solution. The final solution had a viscosity of 3.7 Pa s at a measuring temperature of 40° C.

The finished casting solution was poured by means of a casting mold conditioned to 45° C. onto a metal casting roller conditioned to 64° C. to form a film with a thickness of approximately 170 µm. The film, located on the casting roller, was fed through a climate-controlled zone and for approximately 10 s impinged with a climate of 46° C. and 42% relative humidity (dew point approximately 29° C.) before said film was fed into a coagulation bath filled with water conditioned to 64° C. After a residence time of 10 s to form the membrane structure, the film was drawn off from the casting roller by means of a drawing off roller. In subsequent wash baths, the membrane was fixed and extrated in water. The drying of the membrane took place by means of a drum dryer.

The membrane had a thickness of approximately 140 µm, a maximum separating pore of 0.8 µm, determined by means of the bubble point method, and a transmembrane flow of approximately 220 ml/(cm²·min·bar). The membrane had an asymmetric, comparatively fine-pored, sponge-like pore structure across the entire membrane wall with predominantly fine, thin branches. By means of the SEM images, it can be recognized that a layer with very small pores is located in the wall interior, and the pore size increases starting from this layer in the direction of the surfaces (FIG. 30).

The invention claimed is:

1. A hydrophilic, macroporous filtration membrane comprising:
a flat-sheet membrane based on a film-forming hydrophobic first polymer from the group consisting of aromatic sulfone polymers, and a hydrophilic second polymer, the membrane consisting of a first surface, a second surface, and a supporting layer extending between the first and second surfaces and having a three-dimensional sponge-like network structure,
the supporting layer has a first cover layer on the side thereof facing the first surface and a second cover layer on the side thereof facing the second surface, which cover layers are formed integrally with the supporting layer, and
the first and second surfaces have approximately oval or circular openings which penetrate the first and second cover layers, respectively, and are connected to the supporting layer, wherein an average diameter of the openings in the first surface and an average diameter of the openings in the second surface differ by a factor of less than 2,
the three-dimensional sponge-like network structure of the supporting layer is made up of thick branches and a continuous pore system, and a predominant proportion of the branches have a diameter of at least 0.5 µm at the thinnest point thereof,
the pores in the supporting layer are larger than the openings in the surfaces, a diameter of the pores in the supporting layer, starting from the first surface cover layer in a direction of the second cover layer, is essentially constant in a first area of the supporting layer over at least 50% of the thickness of the supporting layer, and
the filtration membrane has a thickness in the range between 30 and 200 µm.

2. The macroporous filtration membrane according to claim 1, wherein a porous proportion of the area of the first surface is at least 20%.

3. The macroporous filtration membrane according to claim 2, wherein the porous proportion of the area of the first surface is less than 60%.

4. The macroporous filtration membrane according to claim 1, wherein the first or second cover layer, respectively, has a thickness in the range from 3 to 10 µm.

5. The macroporous filtration membrane according to claim 1, wherein the average diameter of the openings in the second surface is 0.5 to 1.5 times as large as the average diameter of the openings in the first surface.

6. The macroporous filtration membrane according to claim 1, wherein the average diameter of the openings in the second surface lies in the range from 2 to 20 µm.

7. The macroporous filtration membrane according to claim 1, wherein the filtration membrane thickness is in the range from 50 to 150 µm.

8. The macroporous filtration membrane according to claim 1, wherein the filtration membrane has a volume porosity in the range from 65 to 85 vol. %.

9. The macroporous filtration membrane according to claim 1, wherein the filtration membrane has a diameter, $d_{max}$, of a maximum separating pore in the range from 5 to 10 µm as determined by means of the bubble point method.

10. The macroporous filtration membrane according to claim 1, wherein the supporting layer has pores with a diameter of at least 1/10 of the membrane thickness.

11. The macroporous filtration membrane according to claim 1, wherein the filtration membrane has a transmembrane flow, TMF, for water in the range from 700 to 4000 ml/(cm$^2$·min·bar).

12. The macroporous filtration membrane according to claim 1, wherein the filtration membrane has a tensile strength of at least 500 cN/mm$^2$ relative to the cross-sectional area thereof.

13. The macroporous filtration membrane according to claim 1, wherein the aromatic sulfone polymer is a polysulfone or a polyethersulfone.

14. The macroporous filtration membrane according to claim 1, wherein the hydrophilic polymer is selected from the group consisting of a polyvinylpyrrolidone, a polyethylene glycol, a polyvinyl alcohol, a polyglycol monoester, a polysorbate, a polyacrylate, a carboxyl methylcellulose, a polyacrylic acid, or a modification or copolymer of these polymers.

15. An infusion set for administering infusion solutions, comprising a drip chamber and an infusion tube connected to the drip chamber, wherein a membrane according to claim 1 is inserted in the infusion tube in the area of the outlet of the drip chamber.

\* \* \* \* \*